(12) United States Patent
Shikata (10) Patent No.: US 8,697,400 B2
(45) Date of Patent: Apr. 15, 2014

(54) METHOD FOR AMPLIFICATION OF DNA FROM BLOOD SAMPLE AND DNA AMPLIFICATION KIT THEREFOR

(75) Inventor: Masamitsu Shikata, Kyoto (JP)

(73) Assignee: Shimadzu Corporation, Kyoto-shi (JP)

( * ) Notice: Subject to any disclaimer, the term of this patent is extended or adjusted under 35 U.S.C. 154(b) by 516 days.

(21) Appl. No.: 12/637,239

(22) Filed: Dec. 14, 2009

(65) Prior Publication Data
US 2010/0151531 A1    Jun. 17, 2010

(30) Foreign Application Priority Data
Dec. 17, 2008    (JP) .................................. 2008-320748

(51) Int. Cl.
*C12P 19/34*    (2006.01)

(52) U.S. Cl.
USPC ........................................................ 435/91.2

(58) Field of Classification Search
USPC ........................................................ 435/91.2
See application file for complete search history.

(56) References Cited

U.S. PATENT DOCUMENTS

| | | | |
|---|---|---|---|
| 2002/0119465 A1* | 8/2002 | Zhao et al. ........................ | 435/6 |
| 2008/0182312 A1* | 7/2008 | Pack et al. ..................... | 435/183 |
| 2009/0042197 A1 | 2/2009 | Hayashizaki et al. | |

FOREIGN PATENT DOCUMENTS

| | | |
|---|---|---|
| JP | 2003-310265 A | 11/2003 |
| WO | 2007/060949 A1 | 11/2006 |

OTHER PUBLICATIONS

Riken Institute., Riken Yokohoma Institute Genome Science Center, Japan., pp. 1-14, Feb. 2007.*
Klintschar et al., J. Forensic Sci., vol. 45, No. 3, pp. 669-673, 2000.*
Yasumasa Mitani, et al., "Rapid SNP diagnostics using asymmetric isothermal amplification and a new mismatch-suppression technology," Nature Methods, Advance Online Publication, Feb. 18, 2007, pp. 1-6.
Japanese Office Action issued in Japanese Patent Application No. 2008-320748 on Aug. 27, 2013.

* cited by examiner

*Primary Examiner* — Cynthia B Wilder
(74) *Attorney, Agent, or Firm* — Sughrue Mion, PLLC (57) ABSTRACT

A DNA amplification method including: subjecting a blood sample having DNA to be amplified, to a pretreatment using an alkaline aqueous solution under ordinary temperature, so as to extract double-stranded DNA from the blood sample and dissociate the double-stranded DNA into a single-stranded DNA to obtain a blood-derived sample including the single-stranded DNA; preparing an isothermal amplification reaction solution comprising a mixture of the blood-derived sample, a primer, dNTP, a strand-displacing DNA polymerase, a magnesium salt and a buffer, to establish an isothermal amplification reaction system meeting optimum conditions for the strand-displacing DNA polymerase; and amplifying DNA in the isothermal amplification reaction system using the single-stranded DNA as a template.

20 Claims, 7 Drawing Sheets

METHOD FOR AMPLIFICATION OF DNA FROM BLOOD SAMPLE AND DNA AMPLIFICATION KIT THEREFOR

BACKGROUND OF THE INVENTION

1. Field of the Invention

The present invention relates to a method for amplification of DNA from a blood sample, and a DNA amplification kit therefor, and more specifically to a DNA amplification method free of a need for setting a plurality of different process temperatures in a series of steps between a blood sample pretreatment step and a DNA amplification reaction step, and a DNA amplification kit therefor. The present invention is useful for life science researches and in medical diagnostic product-related fields.

2. Description of the Background Art

As a method for amplification of DNA from a blood sample, it is common to extract and purify genomic DNA and then subject the purified DNA to synthesis.

Lately, a SMAP (SMart Amplification Process) method has been being developed which includes the steps of: subjecting a blood sample to a pretreatment including no DNA purification treatment; and then amplifying DNA of the pre-treated sample in an isothermal amplification system using a strand-displacing DNA polymerase to perform SNP typing.

The pretreatment step in the SMAP method includes performing heat denaturation at 98° C. for 3 minutes, using a 50 mM sodium hydroxide aqueous solution (see the following Non-Patent Document 1: Nature Methods, 2007, March; 4(3); 257-262).

[Non-Patent Document 1] Yasumasa Mitani, Alexander Lezhava, Yuki Kawai, Takeshi Kikuchi, Atsuko Oguchi-Katayama, Yasushi Kogo, Masayoshi Itoh, Toru Miyagi, Hideki Takakura, Kanako Hoshi, Chiaki Kato, Takahiro Arakawa, Kazuhiro Shibata, Kenji Fukui, Ryoji Masui, Seiki Kuramitsu, Kazuma Kiyotani, Alistair Chalk, Katsuhiko Tsunekawa, Masami Murakami, Tetsuya Kamataki, Takanori Oka, Hiroshi Shimada, Paul E Cizdziel & Yoshihide Hayashizaki, "Rapid SNP diagnostics using asymmetric isothermal amplification and a new mismatch suppression technology", Nature Methods, 2007. March, Vol. 4, No. 3, pp 257-262.

The strand-displacing DNA polymerase has an optimum temperature at about 60° C. Therefore, in the SMAP method, the amplification step using the strand-displacing DNA polymerase can be performed under an isothermal condition (at about 60° C.) without temperature control of repeatedly increasing and reducing a process temperature as in a PCR (Polymerase Chain Reaction) method.

However, in the SMAP method, the blood sample pretreatment step to be performed in advance of the amplification step includes the heat treatment at 98° C.

This means that the SMAP method requires two types of process temperatures: a temperature for causing heat denaturation in the pretreatment step; and an optimum temperature for the strand-displacing DNA polymerase in the amplification step. Thus, it is necessary to provide two temperature control devices each operable to set a respective one of the two process temperatures, or a temperature control device, such as a thermal cycler, operable to change a process temperature.

SUMMARY OF THE INVENTION

There is a need to provide a DNA amplification method without the need for setting a plurality of different process temperatures in a series of steps between a blood sample pretreatment step requiring no DNA purification and a DNA amplification reaction step.

The inventor found that this can be achieved by performing a denaturation treatment in the blood sample pretreatment step, at ordinary temperature, and has achieved the present invention based on this knowledge.

The present invention may have the following features.

(1) According to a first aspect of the present invention, there is provided a method for amplification of DNA from a blood sample, which includes: a pretreatment step of mixing a blood sample having DNA to be amplified, with an alkaline aqueous solution under ordinary temperature, so as to extract double-stranded DNA from the blood sample and dissociate the double-stranded DNA into a single-stranded DNA to obtain a blood-derived sample including the single-stranded DNA;

an isothermal-amplification-reaction-system establishment step of preparing an isothermal amplification reaction solution comprising a mixture of the blood-derived sample, a primer, dNTP, a strand-displacing DNA polymerase, a magnesium salt and a buffer, to establish an isothermal amplification reaction system meeting optimum conditions for the strand-displacing DNA polymerase; and an isothermal amplification step of amplifying DNA in the isothermal amplification reaction system using the single-stranded DNA as a template.

Specifically, in the method of the first aspect of the present invention, after subjecting the blood sample to a denaturation treatment as a pretreatment at ordinary temperature, an adequate isothermal amplification reaction system is established, and DNA is amplified using the established isothermal amplification reaction system. In particular, during the step of establishing the adequate isothermal amplification reaction system, the buffer is used to desirably reduce a high pH of the blood-derived sample including the alkaline aqueous solution so as to obtain the amplification reaction solution having a pH meeting an optimum condition for the strand-displacing DNA polymerase.

In this specification, a plurality of components selected from the group consisting of the primer, the dNTP, the strand-displacing DNA polymerase, the magnesium salt and the buffer will be referred to as "reagent components" or "amplification reaction reagent" for the sake of simplicity, on a case-by-case basis.

(2) Preferably, in the method of this aspect of the present invention, an amount of the alkaline aqueous solution is set to provide an alkali concentration of 50 mM or more in the mixture of the blood sample and alkaline aqueous solution.

As used herein, the term "alkali concentration" means a concentration of hydroxyl ions in a solution.

The use of the alkaline aqueous solution set to provide the above concentration makes it possible to desirably perform the blood sample pretreatment.

(3) Preferably, in the method of this aspect of the present inventions, an amount of the buffer is set to have a concentration of 100 mM or more in the isothermal amplification reaction solution.

The use of the buffer set to have the above concentration makes it possible to sufficiently buffer the amplification reaction system to prevent the alkaline aqueous solution used for the denaturation treatment at ordinary temperature in the pretreatment step from hindering an activity of the strand-displacing DNA polymerase, so as to stably maintain the optimum pH for the enzyme.

(4) In the method of this aspect of the present invention, each of the primer, the dNTP, the strand-displacing DNA polymerase, the magnesium salt and the buffer may be provided in a form contained in water.

In this case, the amplification reaction reagent is provided in a liquid form.

(5) Alternatively, in this aspect of the present invention each of the primer, the dNTP, the strand-displacing DNA polymerase, the magnesium salt and the buffer may be provided in a dry form.

In this case, the amplification reaction reagent is provided in a dry form. This dry reagent may be a freeze-dried product obtained from the above liquid reagent.

(6) Preferably, in this aspect of the present invention, the isothermal-amplification-reaction-system establishment step includes the sub-steps of: preliminarily mixing the blood-derived sample with a buffer aqueous solution; and mixing at least the primer, the dNTP, the strand-displacing DNA polymerase, the magnesium salt and the buffer each provided in a dry form, with the obtained mixture to prepare the isothermal amplification reaction solution.

The above method is designed on the assumption that the amplification reaction reagent is provided in a dry form. In this method, it is preferable that a sum of an amount of the buffer in the buffer aqueous solution (i.e., buffer solution) preliminarily mixed with the blood-derived sample, and an amount of the buffer subsequently added, is set to provide a concentration of 100 mM or more in the section (3).

(7) Preferably, in the method of this aspect of the present invention, the buffer is a tris(hydroxymethyl)aminomethane salt.

(8) Preferably, in the method of this aspect of the present invention, the alkaline aqueous solution is a sodium hydroxide aqueous solution.

(9) According to a second aspect of the present invention, there is provided a kit for use in the method set forth in any one of the sections (1) to (8), which includes the primer, the dNTP, the strand-displacing DNA polymerase, the magnesium salt and the buffer.

(10) In the kit of this aspect of the present invention), each of the primer, the dNTP, the strand-displacing DNA polymerase, the magnesium salt and the buffer may be provided in a dry form.

In this case, the kit may include the dry reagent set forth in the sections (5) and (6), as one item.

As above, this aspect of the present invention can provide a DNA amplification method free of a need for setting a plurality of different process temperatures in a series of steps between a blood sample pretreatment step requiring no DNA purification and a DNA amplification reaction step.

Specifically, in this aspect of the present invention, in the series of steps between the pretreatment step and the amplification reaction step, the process temperature may be set to an optimum value for the strand-displacing DNA polymerase, only once in advance of initiation of the amplification step. Thus, in cases where the method of the present invention is implemented by an apparatus designed to perform the series of steps under automatic control, temperature control means of the apparatus can be composed only of a mechanism for setting a process temperature to a specific value and maintain the set temperature.

DESCRIPTION OF THE EXEMPLARY EMBODIMENTS

A method of an exemplary embodiment of the present invention includes the step of performing a blood sample pretreatment at ordinary temperature (i.e., a pretreatment step; the following Section [I]), the step of establishing an isothermal amplification reaction system from a resulting pretreated solution (i.e., an isothermal-amplification-reaction-system establishment step; the following Section [II]), and the step of performing an amplification reaction (i.e., an isothermal amplification step; the following Section [III])

[I. Pretreatment Step]

In the pretreatment step, a blood sample is mixed with an alkaline aqueous solution, and left at rest or stirred at ordinary temperature to obtain a blood-derived sample. The blood-derived sample can be a target to be subjected to the after-mentioned amplification step, without performing DNA purification.

In the exemplary embodiment of the present invention, the "blood sample pretreatment" means a treatment to be preliminarily performed in advance to allow a nucleic-acid amplification reaction. More specifically, the blood sample pretreatment includes: extracting genome DNA from a DNA-containing body included in a blood sample to isolate the genome DNA outside the DNA-containing body; and dissociating a double-stranded structure of genome DNA into a single-stranded structure.

The DNA-containing body included in a blood sample is not particularly limited, but may be of any type, regardless of whether it is included in blood before or after birth, or mixed into blood from the outside due to infection, etc. For example, the DNA-containing body may include white blood cell, bacterium, fungus and virus.

(I-1. Blood Sample)

Typically, whole blood is used as a blood sample. The whole blood may be of any type, regardless of whether it is subjected to a treatment using an anticoagulant. The blood sample may be any one of fresh blood, stored blood and dried blood, as long as DNA is contained therein. The stored blood may be any type, regardless of chilled storage or frozen storage. An individual as a source of the blood sample includes a human and an animal.

(I-2. Alkaline Aqueous Solution)

In the exemplary embodiment of the present invention, the blood sample pretreatment is performed in an alkaline aqueous solution. The alkaline aqueous solution is not particularly limited, as long as it includes a solute made of a material exhibiting alkaline properties in the form of an aqueous solution. Preferably, the alkaline aqueous solution is a type exhibiting strong alkaline properties, such as an aqueous solution of alkali metal hydroxide or an aqueous solution of alkaline earth metal hydroxide.

In the exemplary embodiment of the present invention, it is preferable to use an alkali metal hydroxide, particularly a sodium hydroxide. However, the solute is not limited thereto, but any other suitable alkali metal hydroxide (e.g., potassium hydroxide) or alkaline earth metal hydroxide may be used. The above solutes may be used independently or in a combination of two or more thereof.

In the exemplary embodiment of the present invention, the alkaline aqueous solution is used at a concentration which allows the blood sample pretreatment to be performed at ordinary temperature. The concentration allowing the blood sample pretreatment to be performed at ordinary temperature is greater than that used in a blood sample pretreatment under heating which has heretofore been widely performed.

More specifically, given that a pretreated mixture obtained through the pretreatment in the exemplary embodiment of the present invention is mixed with a conventional isothermal amplification reaction solution, the concentration of the alkaline aqueous solution for use in the exemplary embodiment of the present invention can be said to be high enough to inhibit an activity of a strand-displacing DNA polymerase in the conventional isothermal amplification reaction solution.

In other words, given that a pretreated mixture obtained through the pretreatment in the exemplary embodiment of the present invention is mixed with a conventional isothermal amplification reaction solution, the concentration of the alkaline aqueous solution for use in the exemplary embodiment of the present invention is high enough to suppress a buffering effect of a buffer contained in the conventional isothermal amplification reaction solution (at a concentration (typically, 10 to 20 mM) for establishing an optimum condition for a strand-displacing DNA polymerase in the conventional isothermal amplification reaction solution).

A specific concentration of the alkaline aqueous solution for use in the exemplary embodiment of the present invention is not particularly limited, as long as it is a relatively high value allowing the ordinary-temperature pretreatment. For example, an alkali concentration may be set at 100 mM or more, preferably 125 mM or more, more preferably 150 mM or more. If the concentration is less than 100 mM, the ordinary-temperature pretreatment is liable to become less able to be achieved. As used herein, the term "alkali concentration" means a concentration of hydroxyl ions in the solution.

An upper limit of the concentration of the alkaline aqueous solution is not particularly limited. For example, the upper limit of the alkali concentration may be preferably set at about 500 mM. If the concentration is greater than 500 mM, an after-mentioned isothermal amplification reaction system is liable to become less able to be established.

An amount of the alkaline aqueous solution is not particularly limited, as long as it is set to allow the alkali concentration in the mixture of the blood sample and the alkaline aqueous solution to have a relatively high value allowing the ordinary-temperature pretreatment. For example, the amount may be set to provide an alkali concentration of 50 mM or more, preferably 62.5 mM or more, more preferably 75 mM or more, or may be set to provide an alkali concentration of 90 mM or more, preferably 112.5 mM or more, more preferably 135 mM or more. If the concentration is less than the lower limit, the ordinary-temperature pretreatment is liable to become less able to be achieved.

An upper limit of the concentration is not particularly limited. For example, the upper limit may be set at 450 mM or 250 mM. If the upper limit is greater than the value, the after-mentioned isothermal amplification reaction system is liable to become less able to be established.

As one example, in a sodium hydroxide aqueous solution having an alkali concentration of 150 mM, an amount of the sodium hydroxide aqueous solution may be set to fall in the range of 1 to 9 µL with respect to 1 µL of the blood sample.

The alkali concentration allowing the ordinary-temperature pretreatment can vary depending on a target sequence. Thus, the amount of the alkaline aqueous solution may be appropriately increased or reduced in consideration of a target sequence to adjust a concentration thereof using the value in the above example as a reference value. Generally, in the adjustment, parameters concerning properties unique to a target nucleic acid sequence and having an impact on amplification efficiency, such as a GC content, a base length and a specific unique sequence, are considered by a person skilled in the art.

(I-3. Pretreatment Conditions)

A temperature of the pretreatment is ordinary temperature. In the exemplary embodiment of the present invention, the ordinary temperature may be any temperature causing no heat denaturation in the blood sample. Specifically, the ordinary temperature is in the range of about 15 to 40° C., preferably in the range of 20 to 35° C., more preferably in the range of 23 to 30° C. Typically, the ordinary temperature is about 25° C.

The pretreatment performed at ordinary temperature makes it possible to achieve a DNA amplification method free of a need for setting a plurality of different process temperatures in a series of steps between the blood sample pretreatment to the DNA amplification reaction step.

A time-period of the pretreatment is not particularly limited. For example, the time-period may be set in the range of 1 to 15 minutes, preferably in the range of 3 to 5 minutes. If the time-period is less than the lower limit of the range, the ordinary-temperature pretreatment is liable to become less able to be achieved. If the time-period is greater than the upper limit of the range, the after-mentioned isothermal amplification reaction system is liable to become less able to be established.

[II. Isothermal-Amplification-Reaction-System Establishment Step]

In an isothermal-amplification-reaction-system establishment step, an adequate isothermal amplification reaction system is established from the blood-derived sample obtained through the pretreatment, without subjecting the blood-derived sample to a DNA purification treatment.

The "adequate isothermal amplification reaction system" means a system capable of initiating and promoting an isothermal amplification reaction while keeping an activity of a strand-displacing DNA polymerase from being inhibited. Establishing an isothermal amplification reaction system means to establish the adequate isothermal amplification reaction system in such a manner that components to be contained in the isothermal amplification reaction system are appropriately determined by a person skilled in the art based on qualitative and quantitative aspects to meet optimum conditions for a strand-displacing DNA polymerase so as to prepare an isothermal amplification reaction solution capable of initiating and promoting an isothermal amplification reaction.

The "isothermal amplification reaction solution" means a mixture of the blood-derived sample and an isothermal amplification reaction reagent.

The optimum conditions comprise at least two parameter concerning pH and temperature. According to need, the optimum conditions may further comprise a parameter concerning salt concentration and any other commonly-known parameter.

The "based on qualitative and quantitative aspects" means to take into account pH, temperature, salt concentration, type of buffer, type of salt, target sequence, and presence of other compatible components (e.g., surfactant or impurities). Particularly, in the exemplary embodiment of the present invention, it is necessary to take into account the presence of the high-concentration alkaline aqueous solution used in the pretreatment. Based on this consideration, it is required to determine an amount of a buffer enough to fully bring out a buffering effect capable of allowing the amplification reaction solution to maintain an optimum pH for a strand-displacing DNA polymerase without being affected by the pH of the high-concentration alkaline aqueous solution (as described in detail in the following Section II-2-3).

(II-1. Form of Isothermal Amplification Reaction Reagent)

The isothermal amplification reaction reagent may be a liquid or dry reagent comprising a plurality of after-mentioned components, i.e., at least a plurality of components selected from the group consisting of a strand-displacing DNA polymerase, a primer, a buffer, dNTP (deoxyribonucleotide triphosphate), and magnesium salt.

(II-1-1. Liquid Reagent)

The liquid reagent can be provided in the form of an aqueous solution containing the selected components. The liquid reagent may be prepared as one type of aqueous solution containing all of the required components, or may be prepared as two or more types of aqueous solutions each containing an appropriately selected part of the required components, wherein the aqueous solutions will be eventually mixed together to allow all of the required components to coexist in the amplification reaction solution. In the case where the liquid reagent is prepared as two or more types of aqueous solutions, how to select ones of the components to be contained in each of the aqueous solutions may be appropriately determined by a person skilled in the art, by taking into account differences in physical properties, such as chemical stability and storage stability, and handleability between the components in the aqueous solution, etc.

(II-1-2. Dry Reagent)

In the dry reagent, the required components are provided in a dry form. For example, the dry reagent can be prepared by freeze-drying a mixture of the above liquid reagent and a freeze-drying agent (stabilizing agent). The dry reagent is desirable in view of superiority in storage stability and handleability of the components. The freeze-drying agent (stabilizing agent) may be sugar alcohol, such as trehalose. The dry reagent may be prepared as one type of freeze-dried product containing all of the required components, or may be prepared as two or more types of freeze-dried products each containing an appropriately selected part of the required components, wherein the freeze-dried products will be eventually mixed together to allow all of the required components to coexist in the amplification reaction solution. In the case where the dry reagent is prepared as two or more types of freeze-dried products, how to select ones of the components to be contained in each of the freeze-dried products may be appropriately determined by a person skilled in the art, by taking into account differences in physical properties, such as chemical stability and storage stability, and handleability between the components in the freeze-dried product and during a freeze-drying process, etc.

The dry reagent may be used in a dry form, or may be used after being converted into a liquid reagent by dissolving it in water or a buffer solution (a buffer contained in this buffer solution forms a part of a buffer for use in the exemplary embodiment of the present invention).

(II-2. Components of Isothermal Amplification Reaction Reagent)

Components of the isothermal amplification reaction reagent are used to establish the isothermal amplification reaction system in coexistence with the blood-derived sample. Specifically, the components of the isothermal amplification reaction reagent includes at least a strand-displacing DNA polymerase, a primer, a buffer, dNTP, and magnesium salt.

(II-2-1. Strand-Displacing DNA Polymerase)

The "strand-displacing DNA polymerase" means an enzyme having a strand displacement activity, i.e., an enzyme capable of, when there is double-stranded DNA in an extension direction during a course of synthesizing complementary DNA strands to a template DNA, continuing the complementary strand synthesis while dissociating the double-stranded DNA.

The strand-displacing DNA polymerase is not particularly limited. For example, the strand-displacing DNA polymerase may be *Bacillus stearothermophilus*-derived large fragment Bst DNA polymerase (Exo (−) Bst (Aliotta et al., Genet. Anal., 12: 185-195 (1996), www.nebj.jp/jp/products/M0275.html), *Bacillus* pallidus-derived Bpa DNA polymerase (U.S. Pat. No. 5,736,373), *Bacillus* acidocaldarius-derived DNA polymerase (JP 2003-274962A), bacteriophage-derived φ29 DNA polymerase (U.S. Pat. Nos. 5,198,543, 5,001,050, Blanco et al.), Exo (−) Bca DNA polymerase (Walker and Linn, Clinical Chemistry 42: 1604-1608 (1996)), phage M2 DNA polymerase (Matsumoto et al., Gene 84: 247 (1989)), phage φ PRD1 DNA polymerase (Jung et al., Proc. Natl. Acad. Sci. USA 84: 8287 (1987)), VENT (TM) DNA polymerase (Kong et al., J. Biol. Chem. 268: 1965-1975 (1993)), Klenow fragment of DNA polymerase I (Jacobsen et al., Eur. J. Biochem. 45: 623-627 (1974)), T5 DNA polymerase (Chatterjee et al., Gene 97: 13-19 (1991)), Sequenase (TM) (produced by US Biochemicals), PRD1 DNA polymerase (Zhu and Ito, Biochem. Biophys. Acta. 1219: 267-276 (1994)), and T4 DNA polymerase holoenzyme (Kaboord and Benkovic, Curr. Biol. 5; 149-157 (1995)). The above enzymes may be used independently or in a combination of two or more thereof.

Based on optimum conditions disclosed in the above documents directed to strand-displacing DNA polymerases, a person skilled in the art can establish the isothermal amplification reaction system in the exemplary embodiment of the present invention.

For example, as one reaction solution providing optimum conditions for large fragment Bst DNA polymerase as one strand-displacing DNA polymerase suitable for the exemplary embodiment of the present invention, there has been known a reaction solution comprising the following composition [: 20 mM Tris-HCl (pH 8.8, 25° C.), 10 mM KCl, 10 mM $(NH_4)_2SO_4$, 2 mM $MgSO_4$, and 0.1% Triton X-100 (www.nebj.jp/jp/products/M0275.html)] and having an optimum temperature of about 60 to 65° C. In the exemplary embodiment of the present invention, the alkaline aqueous solution having a concentration different from that of a conventional alkaline aqueous solution is used in the pretreatment, as mentioned above. Thus, if the pretreated mixture obtained through the pretreatment in the exemplary embodiment of the present invention is mixed with a reaction solution having the above conventional composition, the activity of the strand-displacing DNA polymerase will be inhibited to preclude the establishment of the isothermal amplification reaction system. Therefore, in the exemplary embodiment of the present invention, in the step of establishing the isothermal amplification reaction system, an amount of each of the components of the amplification reagent is appropriately determined to allow the strand-displacing DNA polymerase to be placed under optimum conditions even in the presence of the alkaline aqueous solution used in the pretreatment. For example, as for magnesium salt, potassium salt or surfactant etc. in the components of the amplification reagent, an amount thereof may be set at a value or in a range approximately equal to that in the conventional isothermal amplification reaction reagent. Differently, as for the buffer in the components of the amplification reagent, an amount thereof for establishing the isothermal amplification reaction system is appropriately determined in consideration of the presence of the alkaline aqueous solution used in the pretreatment (as described in detail in the following Section II-2-3).

Thus, in the case where large fragment Bst DNA polymerase is used as the strand-displacing DNA polymerase, a large fragment Bst DNA polymerase-based isothermal amplification reaction system can be established in such a manner that an amount of KCl, $MgSO_4$ or Triton X-100 is set at a value or in a range approximately equal to the conventional amount, and an amount of Tris-HCl is set at a value largely different from the conventional amount to allow the reaction system to be maintained at an optimum pH.

Therefore, an amount of the strand-displacing DNA polymerase is not particularly limited, but may be appropriately determined to allow the isothermal amplification reaction system to be established. For example, an amount of the strand-displacing DNA polymerase may be set to have a concentration of 200 to 1000 U/mL, preferably 400 to 800 U/mL, in the isothermal amplification reaction solution. If the concentration is less than the lower limit of the range, the isothermal amplification reaction system is liable to become less able to be established.

A required amount of the strand-displacing DNA polymerase can vary depending on a target sequence. Thus, the amount of the strand-displacing DNA polymerase may be appropriately increased or reduced in consideration of a target sequence to adjust a concentration thereof using the value in the above example as a reference value. Generally, in the adjustment, parameters concerning properties unique to a target nucleic acid sequence and having an impact on amplification efficiency, such as a GC content, a base length and a specific unique sequence, are considered by a person skilled in the art. More specifically, for example, when a target sequence has a relatively high GC content (e.g., 70% or more, although this value is appropriately determined by a person skilled in the art), the amount of the strand-displacing DNA polymerase may be adjusted by gradually shifting the upper limit of the range in the above example toward a high-concentration side as the GC content becomes higher.

(II-2-2. Primer)

A primer design may be appropriately performed by a person skilled in the art, and thereby the primer is not particularly limited. A person skilled in the art may perform the primer design based on a primer for use in a conventional isothermal amplification method. For example, the conventional isothermal amplification method includes a SMAP (SMart Amplification Process) method, an SDA (Standard Displacement Amplification) method, and a LAMP (Loop-mediated Isothermal Amplification) method.

When a person skilled in the art performs the primer design based on a primer for use in the conventional isothermal amplification method, the same primer as that for use in the conventional isothermal amplification method may be employed. If there is a component required in connection with the use of the primer, such a component may be appropriately selected by a person skilled in the art.

An amount of the primer is not particularly limited. A plurality of types of primers are used in one reaction, and respective concentrations of the primers are different from each other depending on functions thereof. Thus, the amount of the primer may be determined by a person skilled in the art, depending on a desired isothermal amplification reaction system. For example, an amount of the primer may be set to have a concentration of 0.1 to 5 µM, preferably 0.25 to 2 µM, in the isothermal amplification reaction solution. If the concentration is less than the lower limit of the range, the isothermal amplification reaction system is liable to become less able to be established. Further, if the concentration is greater than the upper limit of the range, the isothermal amplification reaction system is liable to become less able to be established.

(II-2-3. Buffer)

A type of the buffer is not particularly limited, but any buffer admissible in the fields of molecular biology and nucleic acid-related chemistry may be used.

For example, the buffer may include: a salt of an acid selected from the group consisting of citric acid, succinic acid, phosphoric acid, carbonic acid, lactic acid, boric acid, cacodylic acid, acetic acid, veronal acetic acid, collidine, hydrochloric acid, glutaric acid and malic acid; a base-addition salt of HEPES (4-(2-hydroxyethyl)-1-piperazineethanesulfonic acid), and an acid-addition salt of Tris (tris(hydroxymethyl)aminomethane) or MOPS (3-(N-morpholino)propanesulfonic acid). In the exemplary embodiment of the present invention, it is preferable to use an acid-addition salt of Tris (tris(hydroxymethyl)aminomethane).

In cases where the salt of the above acid is used, the buffer may be specifically a salt of the acid in the above example and a strong base (e.g., sodium salt or potassium salt).

In cases where the base-addition salt is used, the buffer may be specifically a base-addition salt in which a strong base (such as potassium hydroxide or sodium hydroxide) is added to HEPES (4-(2-hydroxyethyl)-1-piperazineethanesulfonic acid). More specifically, the buffer may be HEPES-KOH.

In cases of the acid-addition salt, the buffer may be specifically an acid-addition salt in which a strong acid (such as hydrochloric acid) and/or a weak acid (such as acetic acid, ethylenediamine tetraacetic acid, boric acid or phosphoric acid) are added to Tris (tris(hydroxymethyl)aminomethane). More specifically, the buffer may be Tris-HCl (tris(hydroxymethyl)aminomethane hydrochloride), TE (tris-EDTA buffer solution), or THE (Tris-sodium chloride-EDTA).

The above buffers may be used independently or in a combination of two or more thereof.

The reaction reagent in the exemplary embodiment of the present invention may be in the form of a liquid reagent or may be in the form of a dry reagent, as mentioned above. In the liquid reagent, the buffer may be provided as a buffer solution containing the buffer. In this case, according to the optimum conditions for the strand-displacing DNA polymerase, a person skilled in the art may appropriately adjust and determine a pH of the buffer solution containing the buffer. For example, the pH may be adjusted in the range of 8 to 9.

In consideration of the presence of the high-concentration alkaline aqueous solution used in the pretreatment, a concentration of the buffer for use in the exemplary embodiment of the present invention has to be set at a value enough to bring out a buffering effect capable of allowing the amplification reaction solution to maintain an optimum pH for the strand-displacing DNA polymerase without being affected by the pH of the high-concentration alkaline aqueous solution. Specifically, the blood-derived sample including the alkaline aqueous solution used in the pretreatment has a high pH value. However, in the amplification reaction solution obtained by mixing the blood-derived sample with the amplification reaction reagent, the pH value has to be sufficiently reduced to the optimum condition for the strand-displacing DNA polymerase. The exemplary embodiment of the present invention, the buffer is used at a concentration sufficient to obtain such an amplification reaction solution. This sufficient concentration is greater than that which has been widely used in the conventional amplification reaction system.

A specific amount of the buffer is not particularly limited, but may be appropriately determined by a person skilled in the art, in such a manner as to allow the adequate isothermal amplification reaction system to be established. For example, on a assumption that an amount of the strand-displacing DNA polymerase is set to have a concentration of 400 to 600 U/mL in the isothermal amplification reaction solution and/or a concentration of the alkaline aqueous solution is set to be 100 mM or more, the amount of the buffer may be set to have a concentration of 100 mM or more, preferably 150 mM or more, more preferably 200 mM or more, in the isothermal amplification reaction solution. An upper limit of the concentration is not particularly limited. For example, the upper limit may be set at about 400 mM or about 500 mM.

If the concentration is less than the lower limit, the buffering effect is liable to become less able to be brought out, and thereby conditions of the isothermal amplification reaction solution are liable to deviate from the optimum conditions for the enzyme. Further, if the concentration is greater than the upper limit, the isothermal amplification reaction system is liable to become less able to be established.

As mentioned in the Section II-2-1, a required amount of the strand-displacing DNA polymerase varies depending on a target sequence. Thus, the above assumption can change in any manner. Consequently, the concentration range of the buffer in the above example can change. For example, in cases where an amount of the strand-displacing DNA polymerase is set to have a concentration less than the lower limit of the range in the above assumption, the amount of the buffer may be set to have a concentration less than 100 mM, after taking into account the concentration of the alkaline aqueous solution used in the pretreatment.

(II-2-4. dNTP)

The "dNTP" is a generic term of four types of deoxyribonucleoside triphosphates (dATP, dCTP, dGTP, dTTP). Depending on an intended purpose of the exemplary embodiment of the present invention, the deoxyribonucleoside triphosphate may be a type subjected to labeling and/or modification to be appropriately performed by a person skilled in the art. In the exemplary embodiment of the present invention, the term "dNTP" also includes such modified or labeled deoxyribonucleoside triphosphates.

Each of the deoxyribonucleoside triphosphates may be used in the same amount, or may be used in a different amount, for example, depending on a nucleic acid sequence.

An amount of the dNTP is not particularly limited, but may be appropriately determined to allow the adequate isothermal amplification reaction system to be established. For example, the amount of the dNTP may be set to have a concentration of 1 to 3 mM, preferably 1 to 2 mM, in the isothermal amplification reaction solution. If the concentration is less than the lower limit of the range, the isothermal amplification reaction system is liable to become less able to be established. Further, if the concentration is greater than the upper limit of the range, the isothermal amplification reaction system is liable to become less able to be established.

(II-2-5. Magnesium Salt)

The magnesium salt is conducive to stability of a double strand between the primer and a DNA template. A type of the magnesium salt is not particularly limited, but may be any type which has heretofore been used for such a purpose. For example, magnesium sulfate or magnesium chloride may be used.

These magnesium salts may be used independently or in a combination of two or more thereof.

An amount of the magnesium salt is not particularly limited, but may be appropriately determined to allow the adequate isothermal amplification reaction system to be established. For example, the amount of the magnesium salt may be set to have a concentration of 6 to 10 mM, preferably 7.5 to 8.5 mM, in the isothermal amplification reaction solution. If the concentration is less than the lower limit of the range, the primer is less likely to be annealed, which causes deterioration in amplification efficiency. Further, if the concentration is greater than the upper limit of the range, non-specific amplification is liable to occur due to increase in mismatch stability.

(II-2-6. Additional Component)

Potassium Salt—An additional component which may be comprised in the isothermal amplification reaction reagent includes potassium salt. The potassium salt can be used for adjusting a salt concentration in the reaction system. A type of the potassium salt is not particularly limited, but may be any type which has heretofore been used for such a purpose. For example, potassium chloride or potassium sulfide may be used. These potassium salts may be used independently or in a combination of two or more thereof.

An amount of the potassium salt is not particularly limited, but may be appropriately determined to avoid hindering the adequate isothermal amplification reaction system. For example, the amount of the potassium salt may be set to have a concentration of 5 to 20 mM, preferably 10 to 12 mM, in the isothermal amplification reaction solution.

Detection Label—A detection label may also be comprised in the isothermal amplification reaction reagent. The label may be contained in the isothermal amplification reaction reagent in such a manner that it is bound to any of the above reagent components (e.g., the primer), or may be contained independently of the above reagent components.

A type of the label is not particularly limited, but may be any type which has heretofore been used in a nucleic acid detection technique for checking the presence of a nucleic acid or a specific sequence based on detection of a signal, regardless of an RI (radioisotope) type or a non-RI type.

In the RI label, any labeling method may be used, regardless of a primer labeling method or a labeling method of incorporating RI-labeled nucleotide into an amplified product.

In the non-RI label, any type of label may be used, regardless of a fluorescent label or an enzyme label. In the exemplary embodiment of the present invention, it is preferable to employ the fluorescent label. For example, the fluorescent label may include fluorescein-based dye, cyanine-based dye and a rhodamine-based dye.

These labels may be used independently or in a combination of two or more thereof.

Surfactant—A surfactant may further be comprised in the isothermal amplification reaction reagent. The surfactant can be used for solubilizing and stabilizing the reaction solution. A type of the surfactant is not particularly limited, but may be any type which has heretofore been used for such a purpose, regardless of an ionic type or a non-ionic type. For example, Tween® 20 or Triton®-X100 may be used.

These surfactants may be used independently or in a combination of two or more thereof.

An amount of the surfactant is not particularly limited, but may be appropriately determined to avoid hindering the adequate isothermal amplification reaction system. For example, the amount of the potassium salt may be set to have a concentration of 0.01 to 0.5% (v/v), preferably 0.05 to 0.2% (v/v), in the isothermal amplification reaction solution.

Freeze-Drying Agent—In the case where the isothermal amplification reaction reagent is provided as a dry reagent, a freeze-drying agent is comprised in the reagent. A type of the freeze-drying agent is not particularly limited, but may be any conventional type. For example, the freeze-drying agent may be sugar alcohol, such as trehalose. Further, the freeze-drying agent may comprise a single type, or may comprise a combination of two or more types.

An amount of the freeze-drying agent is not particularly limited, but may be appropriately determined to allow the amplification reaction reagent to be freeze-dried, and avoid hindering the adequate isothermal amplification reaction system when it coexists with the other components in the isothermal amplification reaction solution. For example, the amount of the potassium salt may be set to have a concentration of 1 to 5% (v/v), preferably 2 to 3% (v/v), in the isothermal amplification reaction solution.

(II-3. Preparation of Isothermal Amplification Reaction Solution)

The reagent components are mixed with the blood-derived sample to form an isothermal amplification reaction solution. The components of the isothermal amplification reaction reagent may be mixed with the blood-derived sample in such a manner that all of the components to be comprised in the reaction system coexist in the isothermal amplification reaction solution at a time when a reaction is initiated in the isothermal amplification reaction solution. Thus, as long as the blood-derived sample including the high-concentration alkaline aqueous solution is kept from being mixed with the strand-displacing DNA polymerase in the absence of the buffer, an order of mixing the components of the isothermal amplification reaction reagent is not particularly limited, but may be appropriately determined by a person skilled in the art.

A specific amount of each of the reagent components in the isothermal amplification reaction solution is as described above. An amount of the blood-derived sample to be mixed may be set to allow a total amount of the amplification reaction solution to fall in the range of 10 to 100 µL, preferably in the range of 10 to 50 µL, with respect to 1 µL of the blood sample.

(II-3-1. Use of Liquid Reagent)

In cases where the isothermal amplification reaction reagent is a liquid reagent, the blood-derived sample and the amplification reaction reagent may be mixed together to allow each of the concentrations of the blood-derived sample and the reagent components in the isothermal amplification reaction solution to be set at the above value or in the above range.

(II-3-2. Use of Dry Reagent)

In cases where the isothermal amplification reaction reagent is a dry reagent, the dry reagent may be used after being converted into a liquid reagent having the above composition by dissolving it in water or a buffer solution (in this case, a buffer contained in this buffer solution forms a part of the buffer required to exist in the isothermal amplification reaction solution).

Alternatively, the isothermal amplification reaction solution may be prepared by preliminarily mixing the blood-derived sample with a buffer aqueous solution, and then mixing the dry reagent with the obtained mixture.

In the dry form, a buffer in the buffer aqueous solution (i.e., buffer solution) preliminarily mixed with the blood-derived sample forms a part of the buffer required to exist in the amplification reaction solution. Thus, it is preferable that a sum of an amount of the buffer in the buffer aqueous solution preliminarily mixed with the blood-derived sample, and an amount of the buffer subsequently added, is set to provide the concentration described in the Section II-2-3, for example, 100 mM or more.

In the dry form, an amount of the buffer solution to be preliminarily mixed with the blood-derived sample may be set at a value enough to allow a pH value of the blood-derived sample to be preliminarily reduced to a certain pH value (based on the optimum pH for the strand-displacing DNA polymerase). For example, in the mixture of the blood-derived sample and the buffer solution preliminarily mixed therewith, a concentration of the buffer may be set to fall in the range of 100 to 300 mM, preferably in the range of 150 to 200 mM.

[III. Isothermal Amplification Step]

In the isothermal amplification step, DNA is amplified through an isothermal amplification reaction using the reaction system established in the above manner.

The "isothermal amplification reaction" means to perform an amplification reaction at an approximately constant temperature, wherein there is no need to set a plurality of different process temperatures and perform temperature control, differently from an amplification reaction, such as the PCR method, designed to change a process temperature in each of a DNA denaturation step, a primer annealing step and a DNA strand extension step.

(III-1. Reaction Temperature)

A temperature required for performing the amplification reaction is not particularly limited, because it depends on an optimum temperature unique to the strand-displacing DNA polymerase to be used. Thus, the temperature of the amplification reaction is appropriately determined by a person skilled in the art, depending on the strand-displacing DNA polymerase to be used.

Most of the strand-displacing DNA polymerases have no activity at a temperature of less than about 30° C., and exhibit deactivation at a temperature of greater than about 70° C. This means that most of the strand-displacing DNA polymerases have an optimum temperature in the range of 30 to 70° C. or in the range of 35 to 65° C.

For example, large fragment Bst DNA polymerase as one strand-displacing DNA polymerase suitable for the exemplary embodiment of the present invention has an optimum temperature in the range of 60 to 65° C.

In the isothermal amplification step, the amplification reaction is isothermally performed while maintaining an optimum temperature for the strand-displacing DNA polymerase. In the isothermal reaction, although a temperature change occurs unless temperature control is performed to positively change the temperature, such a temperature change is permitted as long as it falls within an optimum temperature range.

(III-2. Reaction Time-Period)

A time-period of the amplification reaction is not particularly limited, but may be appropriately determined by a person skilled in the art. For example, the time-period may be set in the range of 0.25 to 3 hours, preferably in the range of 0.5 to 1 hour.

[IV. Amplification Reaction Reagent Kit]

A kit of an exemplary embodiment of the present invention includes the components described in the Section II. The kit may comprise a liquid reagent as described in the Section II-1-1, or may include a dry reagent as described in the Section II-1-2. The reagent may be used as a combination of two or more types of liquid reagent or dry reagents, as mentioned above. The kit may include such a combination. The kit including the dry reagent may additionally include a buffer to be preliminarily mixed with the blood-derived sample, as described in the Section II-3-2.

Further, the kit may include specific one or more of the reagent components in the form of a liquid reagent, and the remaining reagent components in the form of a dry reagent.

EXAMPLE

The exemplary embodiment of the present invention will be more specifically described by showing an example below. It is understood that the present invention is not limited to the following examples.

Reference Example

In Reference Example 1, under heating, a blood sample was subjected to a pretreatment using a 50 mM NaOH aqueous solution (an NaOH concentration in a mixture of blood and an NaOH aqueous solution was 33.3 mM), and then subjected to an amplification reaction in a reaction solution containing 200 mM Tris Cl.

5 µL of blood collected by a commercially available EDTA blood collecting and stored in a frozen state was mixed with 10 µL of 50 mM NaOH aqueous solution, and the obtained mixture was subjected to a heating treatment at 98° C. for 5 minutes, as a pretreatment. After the heating treatment, the pretreated solution was immersed in ice water and cooled.

4 µL of amplification reaction reagent was added to 1 µL of the blood sample pretreated in the above manner, to obtain an amplification reaction solution.

A composition of the amplification reaction reagent was as follows:

| 0.4 µL | primer set |
| 2.5 µL | reaction buffer |
| 0.2 µL | Bst DNA polymerase (12,000 U/mL) |
| 0.9 µL | water |

As the primer set in the amplification reaction reagent, CYP2C9*3(A), CYP2C9*3(C), VKORC1-1639(G), and VKORC1-1639(A) contained in SmartAmp Warfarin Dosage Test Kit (DNAFORM Inc.) were used.

As the reaction buffer in the amplification reaction reagent, a reaction buffer having the following composition was prepared and used (a reaction buffer in the SmartAmp Warfarin Dosage Test Kit was not used).

| 400 mM | Tris•Cl (pH 8.8) |
| 2.4 mM | dNTPs |
| 16 mM | $MgSO_4$ |
| 20 mM | KCl |
| 0.005% (v/v) | SYBR Green 1 |

A concentration of Tris.Cl in the entire amplification reaction reagent was 200 mM.

The Bst DNA polymerase in the amplification reaction reagent was prepared by diluting Bst DNA polymerase (New England BioLabs inc.) ten times by water.

Figure 1:
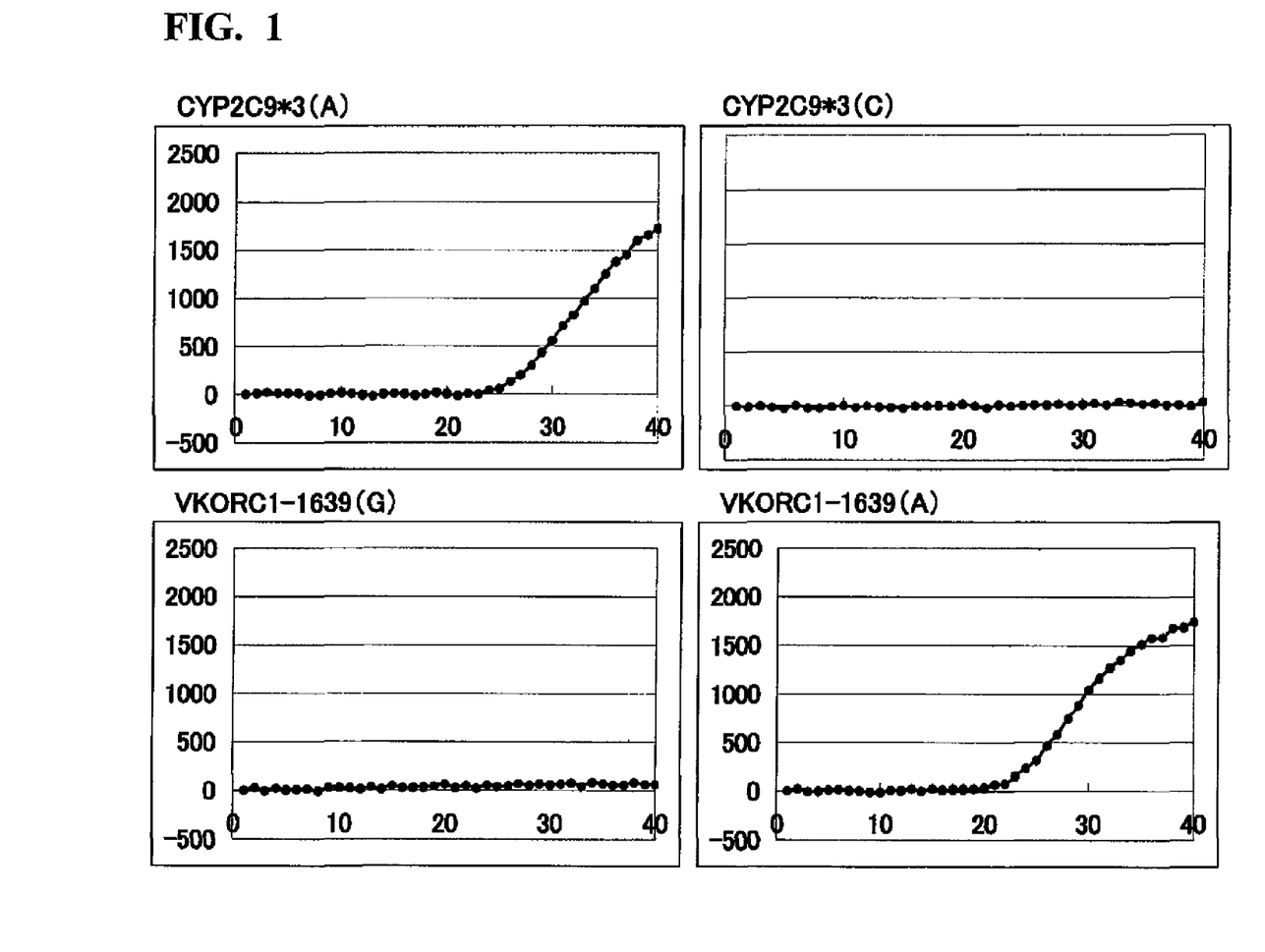
FIG. 1 is a graph showing a genotype detection result obtained in Reference Example 1, wherein, under heating, a blood sample was subjected to a pretreatment using a 50 mM NaOH aqueous solution (an NaOH concentration in a mixture of blood and an NaOH aqueous solution was 33.3 mM), and then subjected to an amplification reaction in a reaction solution containing 200 mM Tris.Cl.

The amplification reaction solution was set in a cycler for quantitative PCR (Mx 3000P, Stratagene Inc.) to measure a fluorescence amount 40 times at intervals of 1 minute at 60° C. FIG. 1 is a graph showing a temporal change of the measured fluorescence amount. In FIG. 1, the horizontal axis represents time (minute), and the vertical axis represents fluorescence amount (a value derived by subtracting a fluorescence amount within 1 minute after initiation of the amplification reaction from each of the measured values) (This is the same in all figures).

As seen in FIG. 1, this blood sample has genotypes: A homo-type for CYP2C9 and A homo-type for VKORC1.

Comparative Example 1

In Comparative Example 1, under heating, a blood sample was subjected to a pretreatment using a 50 mM NaOH aqueous solution (an NaOH concentration in a mixture of blood and an NaOH aqueous solution was 33.3 mM), and then subjected to an amplification reaction in a reaction solution containing 20 mM Tris.Cl.

Figure 2:
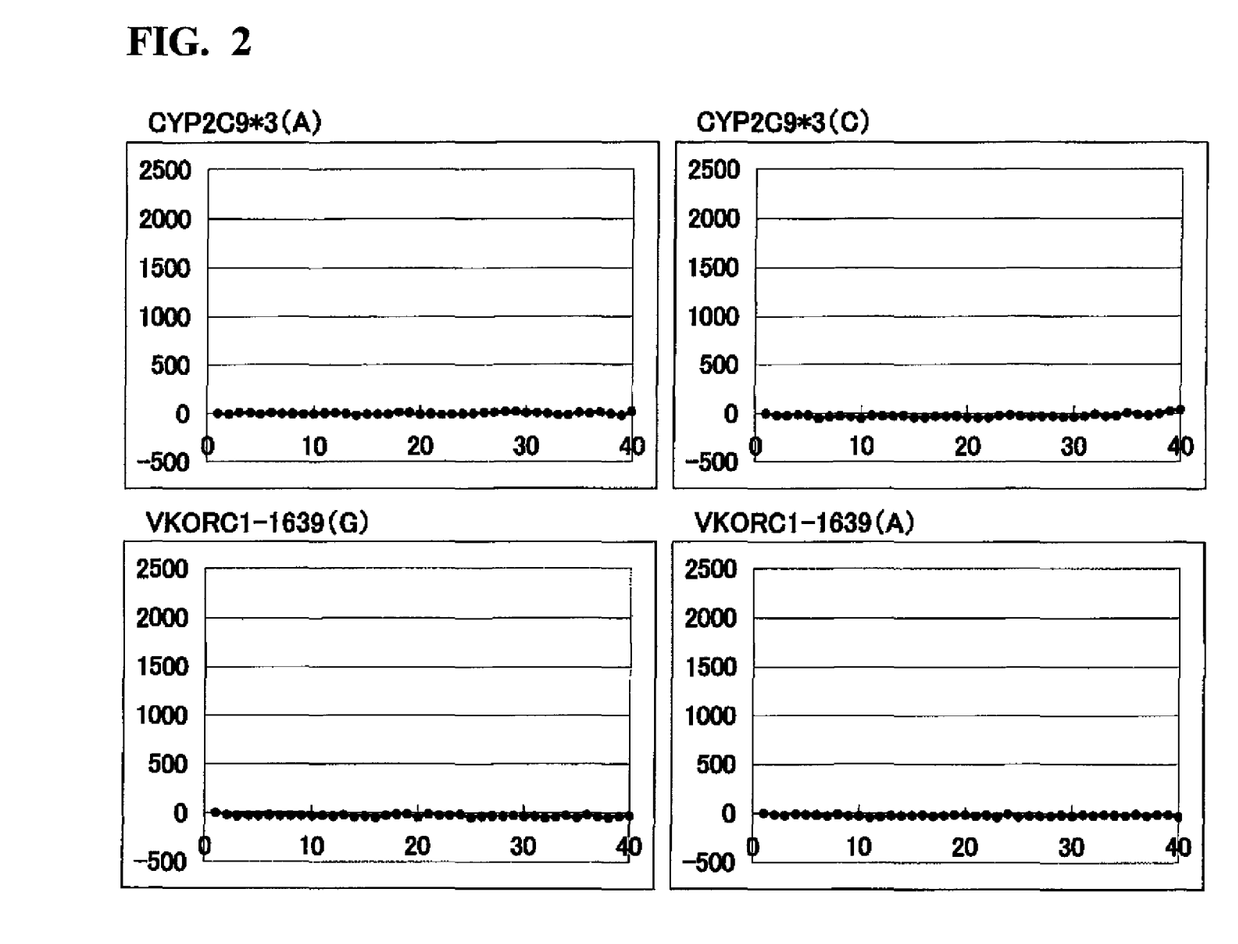
FIG. 2 is a graph showing a genotype detection result obtained in Comparative Example 1, wherein, under heating, a blood sample was subjected to a pretreatment using a 50 mM NaOH aqueous solution (an NaOH concentration in a mixture of blood and an NaOH aqueous solution was 33.3 mM), and then subjected to an amplification reaction in a reaction solution containing 20 mM Tris.Cl.

In other words, except that the reaction buffer was prepared to provide a Tris.Cl concentration of 20 mM in the entire amplification reaction solution, the same operation as that in Reference Example 1 was performed. FIG. 2 shows an obtained result.

As seen in FIG. 2, no genotype could be detected. This shows that the adequate amplification reaction system cannot be established under the conditions in Comparative Example 1.

Comparative Example 2

In Comparative Example 2, under room temperature, a blood sample was subjected to a pretreatment using a 150 mM NaOH aqueous solution (an NaOH concentration in a mixture of blood and an NaOH aqueous solution was 100 mM), and then subjected to an amplification reaction in a reaction solution containing 20 mM Tris.Cl.

Figure 3:
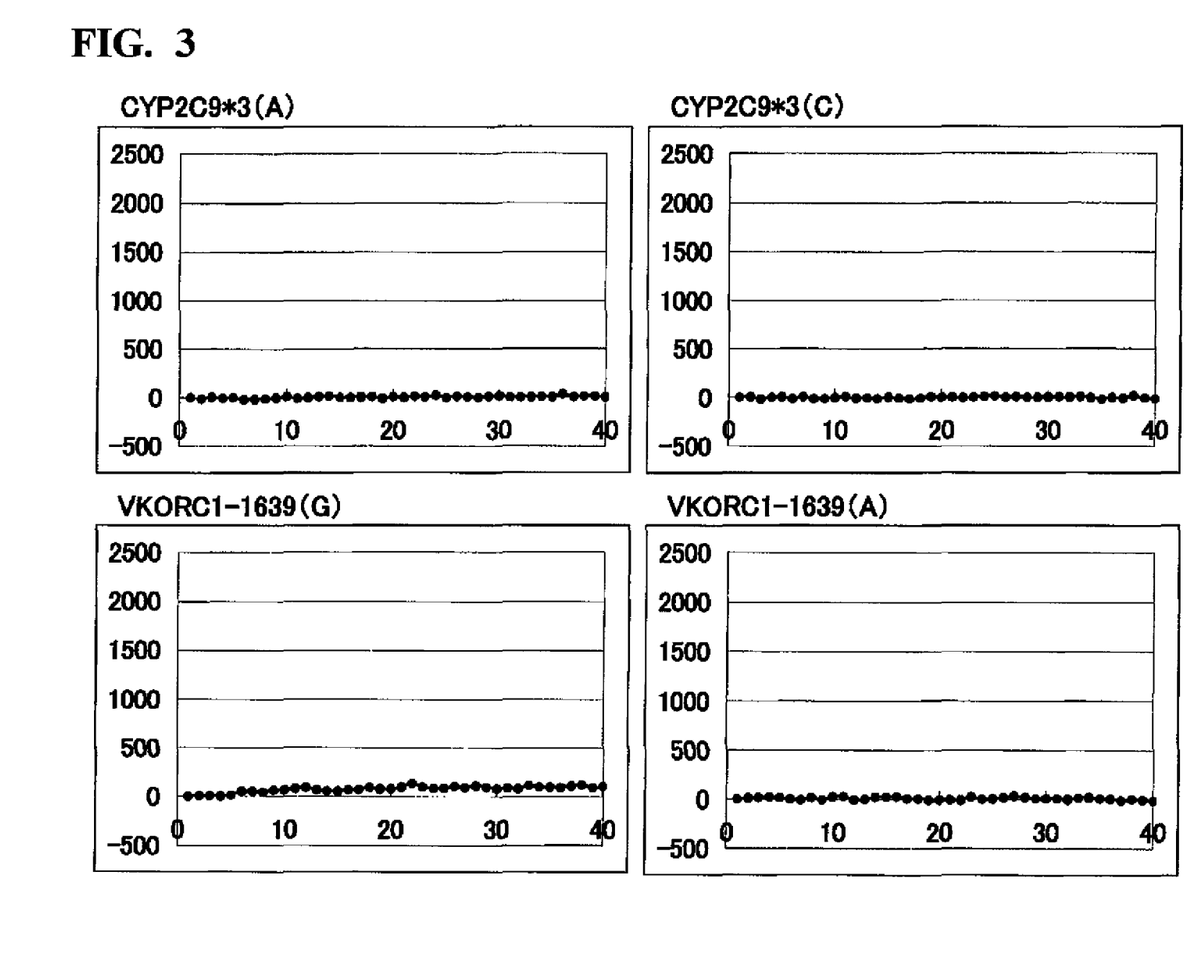
FIG. 3 is a graph showing a genotype detection result obtained in Comparative Example 2, wherein, under room temperature, a blood sample was subjected to a pretreatment using a 150 mM NaOH aqueous solution (an NaOH concentration in a mixture of blood and an NaOH aqueous solution was 100 mM), and then subjected to an amplification reaction in a reaction solution containing 20 mM Tris.Cl.

In other words, except that conditions of the pretreatment were changed in the following point, the same operation as that in Reference Example 1 was performed. 5 μL of blood collected by a commercially available EDTA blood collecting and stored in a frozen state was mixed with 10 μL of 150 nM NaOH aqueous solution, and the obtained mixture was left at rest at room temperature for 5 minutes, as a pretreatment. FIG. 3 shows an obtained result.

As seen in FIG. 3, no genotype could be detected. This shows that the adequate amplification reaction system cannot be established under the conditions in Comparative Example 2.

Comparative Example 3

In Comparative Example 3, under ordinary temperature, a blood sample was subjected to a pretreatment using a 50 mM NaOH aqueous solution (an NaOH concentration in a mixture of blood and an NaOH aqueous solution was 33.3 mM), and then subjected to an amplification reaction in a reaction solution containing 200 mM Tris.Cl.

Figure 4:
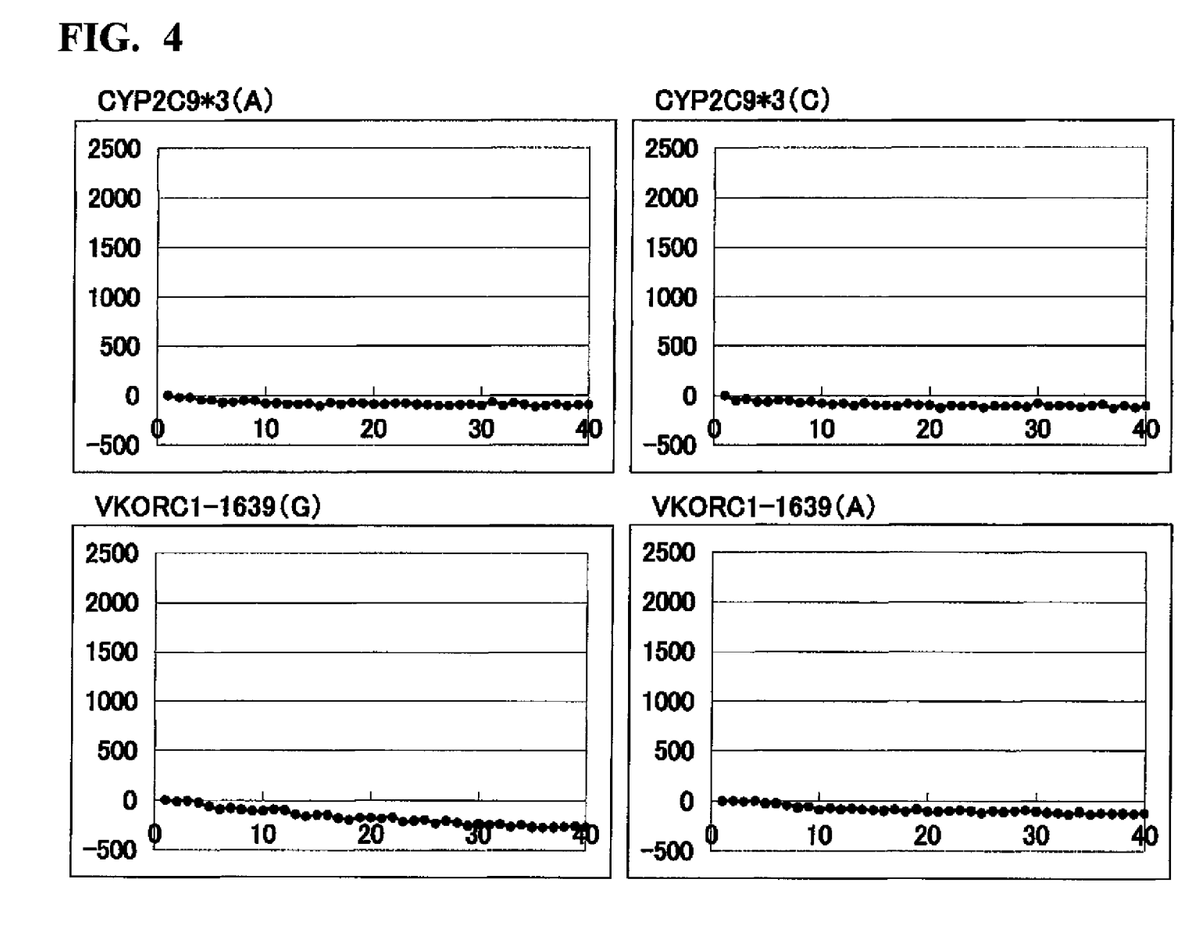
FIG. 4 is a graph showing a genotype detection result obtained in Comparative Example 3, wherein, under ordinary temperature, a blood sample was subjected to a pretreatment using a 50 mM NaOH aqueous solution (an NaOH concentration in a mixture of blood and an NaOH aqueous solution was 33.3 mM), and then subjected to an amplification reaction in a reaction solution containing 200 mM Tris.Cl.

In other words, except that conditions of the pretreatment were changed in the following point, the same operation as that in Reference Example 1 was performed. 5 μL of blood collected by a commercially available EDTA blood collecting and stored in a frozen state was mixed with 10 μL of 50 mM NaOH aqueous solution, and the obtained mixture was left at rest at room temperature for 5 minutes, as a pretreatment. FIG. 4 shows an obtained result.

As seen in FIG. 4, no genotype could be detected. This shows that the adequate amplification reaction system cannot be established under the conditions in Comparative Example 3.

Inventive Example 1

In Inventive Example 1, under ordinary temperature, a blood sample was subjected to a pretreatment using a 100 mM NaOH aqueous solution (an NaOH concentration in a mixture of blood and an NaOH aqueous solution was 66.7 mM), and then subjected to an amplification reaction in a reaction solution containing 200 mM Tris.Cl.

5 μL of blood collected by a commercially available EDTA blood collecting and stored in a frozen state was mixed with 10 μL of 100 mM NaOH aqueous solution, and the obtained mixture was left at rest at room temperature (25° C.) for 5 minutes to perform a pretreatment.

4 μL of amplification reaction reagent was added to 1 μL of the blood sample pretreated in the above manner, to obtain an amplification reaction solution.

A composition of the amplification reaction reagent was as follows:

| | |
|---|---|
| 0.4 μL | primer set |
| 2.5 μL | reaction buffer |
| 0.2 μL | Bst DNA polymerase (12,000 U/mL) |
| 0.9 μL | water |

As the primer set in the amplification reaction reagent, CYP2C9*3(A) (:for reference), CYP2C9*3(C) (:for reference), VKORC1-1639(G), and VKORC1-1639(A) contained in SmartAmp Warfarin Dosage Test Kit (DNAFORM Inc.) were used.

As the reaction buffer in the amplification reaction reagent, a reaction buffer having the following composition was prepared and used (a reaction buffer in the SmartAmp Warfarin Dosage Test Kit was not used).

| | |
|---|---|
| 400 mM | Tris•Cl (pH 8.8) |
| 2.4 mM | dNTPs |
| 16 mM | MgSO$_4$ |
| 20 mM | KCl |
| 0.005% (v/v) | SYBR Green 1 |

A concentration of Tris.Cl in the entire amplification reaction reagent was 200 mM.

The Bst DNA polymerase in the amplification reaction reagent was prepared by diluting Bst DNA polymerase (New England BioLabs inc.) ten times by water.

Figure 5:
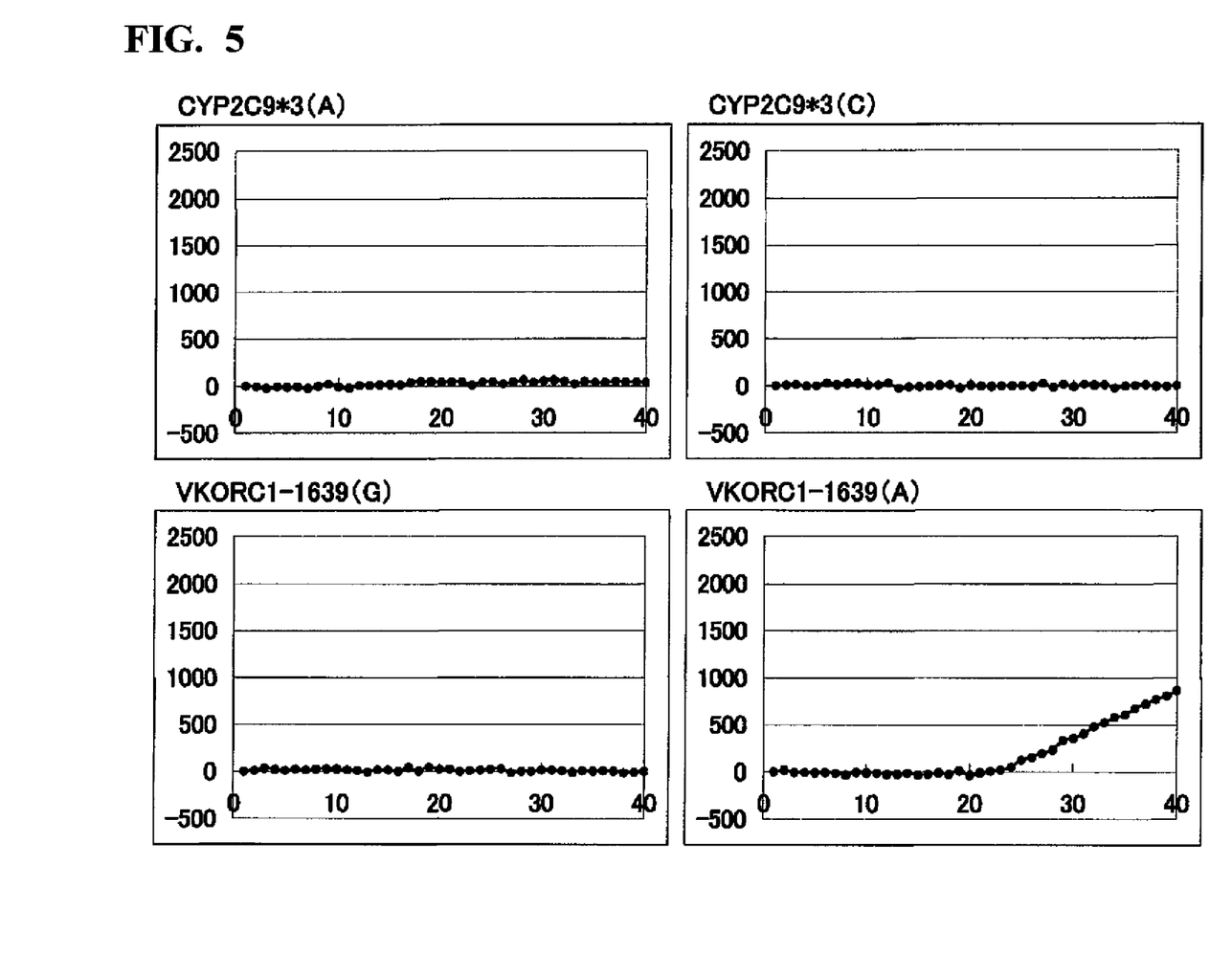
FIG. 5 is a graph showing a genotype detection result obtained in Inventive Example 1, wherein, under ordinary temperature, a blood sample was subjected to a pretreatment using a 100 mM NaOH aqueous solution (an NaOH concentration in a mixture of blood and an NaOH aqueous solution was 66.7 mM), and then subjected to an amplification reaction in a reaction solution containing 200 mM Tris.Cl.

The amplification reaction solution was set in a cycler for quantitative PCR (Mx 3000P, Stratagene Inc.) to measure a fluorescence amount 40 times at intervals of 1 minute at 60° C. FIG. 5 is a graph showing a temporal change of the measured fluorescence amount. In FIG. 5, the horizontal axis represents time (minute), and the vertical axis represents fluorescence amount (a value derived by subtracting a fluorescence amount within 1 minute after initiation of an amplification reaction from each of the measured values) (This is the same in all figures).

As seen in FIG. 5, as to this blood sample, A homo-type for VKORC1 was detected, whereas a genotype for CYP2C9 was not detected. However, after-mentioned Inventive Examples show that a genotype for CYP2C9 can be detected by increasing the NaOH concentration.

Specifically, although the conditions employed in Inventive Example 1 are sufficient to detect only VKORC1 genotype, the detection of CYP2C9 genotype is requited to set the NaOH concentration at a level of those in the after-mentioned Inventive Examples (concentration of greater than 66.7 mM in the mixture, for example 100 mM). Further, even if the NaOH concentration is 66.7 mM in the mixture, CYP2C9 genotype can be detected by adjusting setting of other conditions (e.g., enzyme concentration), in some cases.

FIG. 5 also shows that desirable conditions (e.g., condition of the NaOH concentration) are likely to vary depending on a gene or a base sequence in a target area.

Inventive Example 2

In Inventive Example 2, under ordinary temperature, a blood sample was subjected to a pretreatment using a 150 mM NaOH aqueous solution (an NaOH concentration in a mixture of blood and an NaOH aqueous solution was 100 mM), and then subjected to an amplification reaction in a reaction solution containing 200 mM Tris.Cl.

5 μL of blood collected by a commercially available EDTA blood collecting and stored in a frozen state was mixed with 10 μL of 150 mM NaOH aqueous solution, and the obtained mixture was left at rest at room temperature (25° C.) for 5 minutes to perform a pretreatment.

4 μL of amplification reaction reagent was added to 1 μL of the blood sample pretreated in the above manner, to obtain an amplification reaction solution.

A composition of the amplification reaction reagent was as follows:

| | |
|---|---|
| 0.4 μL | primer set |
| 2.5 μL | reaction buffer |

-continued

| 0.2 µL | Bst DNA polymerase (12,000 U/mL) |
| 0.9 µL | water |

As the primer set in the amplification reaction reagent, CYP2C9*3(A), CYP2C9*3(C), VKORC1-1639(G), and VKORC1-1639(A) contained in SmartAmp Warfarin Dosage Test Kit (DNAFORM Inc.) were used.

As the reaction buffer in the amplification reaction reagent, a reaction buffer having the following composition was prepared and used (a reaction buffer in the SmartAmp Warfarin Dosage Test Kit was not used).

| 400 mM | Tris•Cl (pH 8.8) |
| 2.4 mM | dNTPs |
| 16 mM | $MgSO_4$ |
| 20 mM | KCl |
| 0.005% (v/v) | SYBR Green 1 |

A concentration of Tris.Cl in the entire amplification reaction reagent was 200 mM.

The Bst DNA polymerase in the amplification reaction reagent was prepared by diluting Bst DNA polymerase (New England BioLabs inc.) ten times by water.

Figure 6:
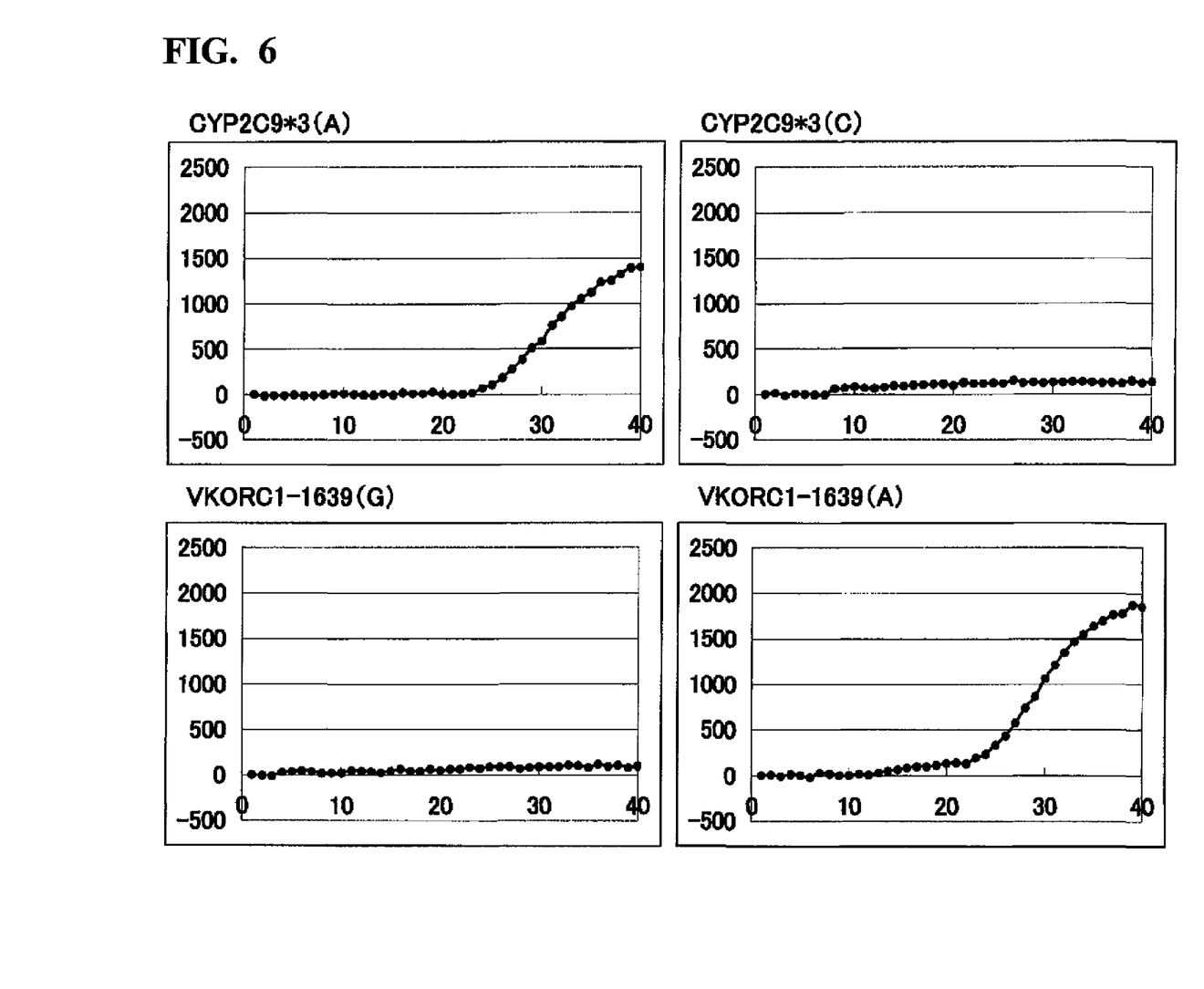
FIG. 6 is a graph showing a genotype detection result obtained in Inventive Example 2, wherein, under ordinary temperature, a blood sample was subjected to a pretreatment using a 150 mM NaOH aqueous solution (an NaOH concentration in a mixture of blood and an NaOH aqueous solution was 100 mM), and then subjected to an amplification reaction in a reaction solution containing 200 mM Tris.Cl.

The amplification reaction solution was set in a cycler for quantitative PCR (Mx 3000P, Stratagene Inc.) to measure a fluorescence amount 40 times at intervals of 1 minute at 60° C. FIG. 6 is a graph showing a temporal change of the measured fluorescence amount. In FIG. 6, the horizontal axis represents time (minute), and the vertical axis represents fluorescence amount (a value derived by subtracting a fluorescence amount within 1 minute after initiation of an amplification reaction from each of the measured values).

As seen in FIG. 6, A homo-type for CYP2C9 was detected, and A homo-type genotype for VKORC1 was detected, as with the result in FIG. 5.

Inventive Example 3

In Inventive Example 3, under ordinary temperature, a blood sample was subjected to a pretreatment using a 150 mM NaOH aqueous solution (an NaOH concentration in a mixture of blood and an NaOH aqueous solution was 100 mM), and then subjected to an amplification reaction in a reaction solution prepared using a dry agent.

5 µl, of blood collected by a commercially available EDTA blood collecting and stored in a frozen state was mixed with 10 µL, of 150 mM NaOH aqueous solution, and the obtained mixture was left at rest at room temperature (25° C.) for 5 minutes to perform a pretreatment.

60 µL of 200 mM Tris Cl (pH 8.8) was added to and mixed with the blood sample pretreated in the above manner.

2.5 µL of the obtained treated solution was added to the dry reagent to obtain an amplification reaction solution.

A composition of the dry was prepared by freeze-drying 2 µL of solution having the following composition, in a reaction tube.

| 0.2 µL | primer set |
| 1.25 µL | reaction buffer |
| 0.1 µL | Bst DNA polymerase (12,000 U/mL) |
| 0.45 µL | water |

As the primer set in the solution, CYP2C9*3(A), CYP2C9*3(C), VKORC1-1639(G), and VKORC1-1639(A) contained in SmartAmp Warfarin Dosage Test Kit (DNAFORM Inc.) were used.

As the reaction buffer in the solution, a reaction buffer having the following composition was prepared and used (a reaction buffer in the SmartAmp Warfarin Dosage Test Kit was not used).

| 40 mM | Tris•Cl (pH 8.8) |
| 2.4 mM | dNTPs |
| 16 mM | $MgSO_4$ |
| 20 mM | KCl |
| 0.005% (v/v) | SYBR Green 1 |

A concentration of Tris.Cl in the entire amplification reaction reagent was 200 mM.

The Bst DNA polymerase in the solution was prepared by diluting Bst DNA polymerase (New England BioLabs inc.) ten times by water.

Figure 7:
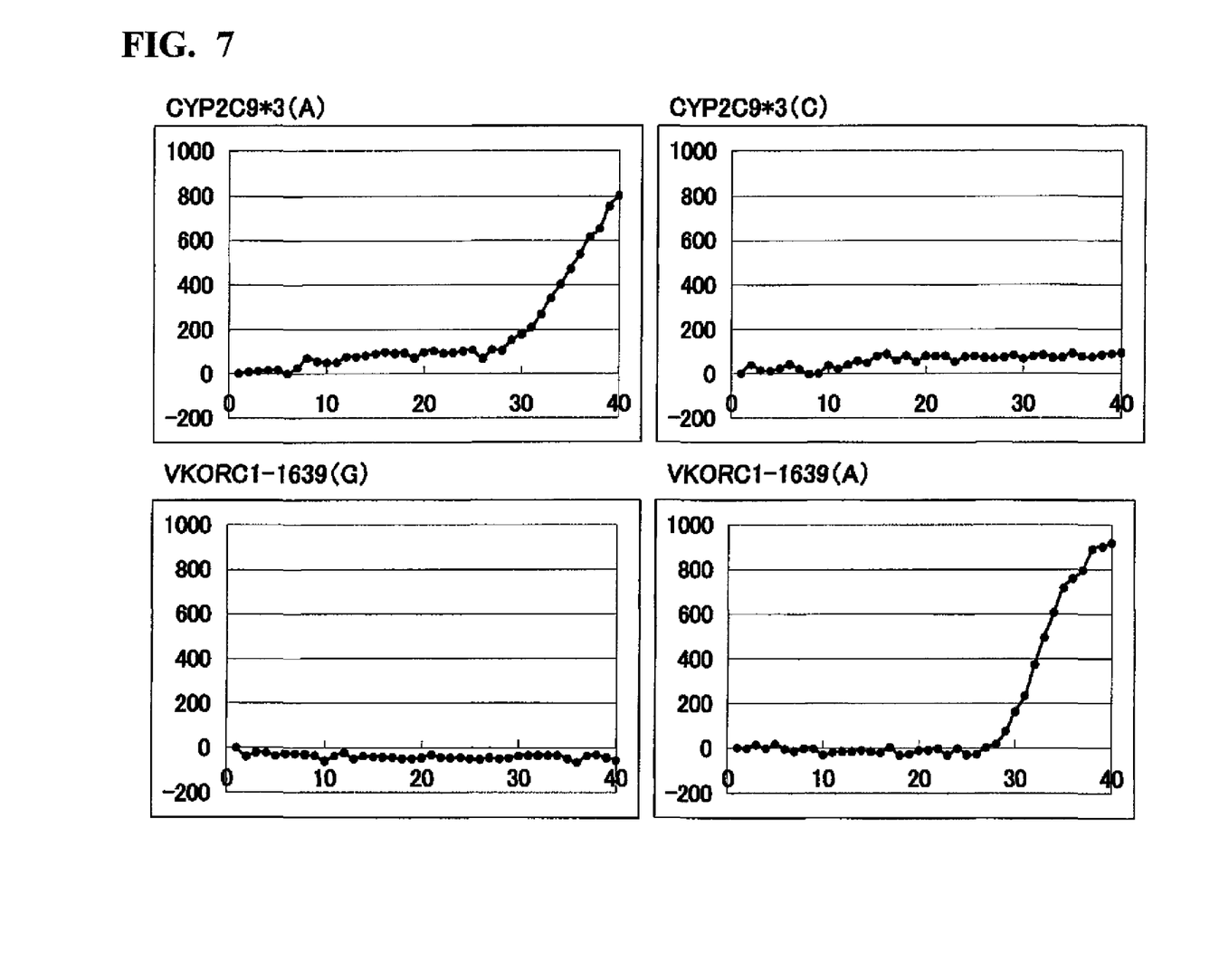
FIG. 7 is a graph showing a genotype detection result obtained in inventive Example 3, wherein, under ordinary temperature, a blood sample was subjected to a pretreatment using a 150 mM NaOH aqueous solution (an NaOH concentration in a mixture of blood and an NaOH aqueous solution was 100 mM), and then subjected to an amplification reaction in a reaction solution prepared using a dry agent.

The amplification reaction solution was set in a cycler for quantitative PCR (Mx 3000P, Stratagene Inc.) to measure a fluorescence amount 40 times at intervals of 1 minute at 60° C. FIG. 7 is a graph showing a temporal change of the measured fluorescence amount. In FIG. 7, a fluorescence amount is shown as a value derived by subtracting a fluorescence amount within 1 minute after initiation of an amplification reaction from each of the measured values.

As seen in FIG. 7, A homo-type genotype for CYP2C9 was detected, as with the result in FIG. 6, and A homo-type for VKORC1 was detected, as with the results in FIGS. 5 and 6.

What is claimed is:

1. A method for amplification of DNA from a blood sample, the method consisting of:
    pretreating a blood sample having DNA to be amplified by mixing the blood sample having DNA to be amplified, with an alkaline aqueous solution under a temperature range between 15° C. and 40° C., so as to extract double-stranded DNA from the blood sample and to dissociate the double-stranded DNA into a single-stranded DNA to obtain a blood-derived sample including the single-stranded DNA;
    preparing an isothermal amplification reaction solution comprising a mixture of the blood-derived sample, a primer, deoxyribonucleotide triphosphate (dNTP), a strand-displacing DNA polymerase, a magnesium salt and a buffer, to establish an isothermal amplification reaction system for the strand-displacing DNA polymerase; and
    amplifying DNA in the isothermal amplification reaction system using the single-stranded DNA as a template.

2. The method as defined in claim 1, wherein the alkaline aqueous solution comprises an alkali concentration of 50 mM or more in the mixture of the blood sample and the alkaline aqueous solution.

3. The method as defined in claim 1, wherein the buffer comprises a concentration of 100 mM or more in the isothermal amplification reaction solution.

4. The method as defined in claim 1, wherein each of the primer, the dNTP, the strand-displacing DNA polymerase, the magnesium salt and the buffer is provided in a form contained in water.

5. The method as defined in claim 1, wherein each of the primer, the dNTP, the strand-displacing DNA polymerase, the magnesium salt and the buffer is provided in a dry form.

6. The method as defined in claim 5, wherein the preparing the isothermal amplification reaction solution includes the sub-steps of:
   preliminarily mixing the blood-derived sample with the buffer aqueous solution; and
   mixing at least the primer, the dNTP, the strand-displacing DNA polymerase, the magnesium salt and the buffer each provided in a dry form, with the preliminarily mixed sample and buffer aqueous solution to prepare the isothermal amplification reaction solution.

7. The method as defined in claim 1, wherein the buffer is a tris(hydroxymethyl)aminomethane salt.

8. The method as defined in claim 1, wherein the alkaline aqueous solution is a sodium hydroxide aqueous solution.

9. The method as defined in claim 2, wherein the buffer comprises a concentration of 100 mM or more in the isothermal amplification reaction solution.

10. The method as defined in claim 2, wherein each of the primer, the dNTP, the strand-displacing DNA polymerase, the magnesium salt and the buffer is provided in a form contained in water.

11. The method as defined in claim 2, wherein each of the primer, the dNTP, the strand-displacing DNA polymerase, the magnesium salt and the buffer is provided in a dry form.

12. The method as defined in claim 3, wherein each of the primer, the dNTP, the strand-displacing DNA polymerase, the magnesium salt and the buffer is provided in a form contained in water.

13. The method as defined in claim 3, wherein each of the primer, the dNTP, the strand-displacing DNA polymerase, the magnesium salt and the buffer is provided in a dry form.

14. The method as defined in claim 5, wherein the buffer is a tris(hydroxymethyl)aminomethane salt.

15. The method as defined in claim 5, wherein the alkaline aqueous solution is a sodium hydroxide aqueous solution.

16. The method as defined in claim 1, wherein the mixed blood sample with the alkaline aqueous solution is maintained under the temperature range between 15° C. and 40° C. before the amplification of the DNA.

17. The method as defined in claim 1, wherein the blood sample having DNA to be amplified is mixed with the alkaline aqueous solution under a temperature range between 20° C. and 35° C.

18. The method as defined in claim 17, wherein the blood sample having DNA to be amplified is mixed with the alkaline aqueous solution under a temperature range between 23° C. and 30° C.

19. The method as defined in claim 1, wherein the buffer comprises a concentration of 200 mM or more in the isothermal amplification reaction solution under the temperature range between 15° C. and 40° C.

20. The method as defined in claim 2, wherein the buffer comprises a concentration of 200 mM or more in the isothermal amplification reaction solution under the temperature range between 15° C. and 40° C.

\* \* \* \* \*